(12) United States Patent
Goerner et al.

(10) Patent No.: US 8,715,594 B2
(45) Date of Patent: May 6, 2014

(54) APPARATUS FOR EMBEDDING TISSUE SAMPLES

(71) Applicant: Thermo Shandon Ltd., Cheshire (GB)

(72) Inventors: Peter Goerner, Great Sutton (GB); Caroline Breen, Chester (GB); Roger Harrington Smith, Manchester (GB); Sheila Christine Dandy, Warrington (GB); Alan Harold Bridge, Prescot (GB)

(73) Assignee: Thermo Shandon Ltd., Cheshire (GB)

( * ) Notice: Subject to any disclaimer, the term of this patent is extended or adjusted under 35 U.S.C. 154(b) by 0 days.

(21) Appl. No.: 13/845,665

(22) Filed: Mar. 18, 2013

(65) Prior Publication Data
US 2013/0217109 A1  Aug. 22, 2013

Related U.S. Application Data

(62) Division of application No. 12/889,843, filed on Sep. 24, 2010, now Pat. No. 8,486,351.

(30) Foreign Application Priority Data

Sep. 25, 2009 (GB) .................... 0916919.4

(51) Int. Cl.
*A61B 10/00* (2006.01)

(52) U.S. Cl.
USPC ........... 422/536; 422/500; 422/501; 422/560; 422/565

(58) Field of Classification Search
USPC .................. 422/50, 536, 500–501, 560, 565; 436/174
See application file for complete search history.

(56) References Cited

U.S. PATENT DOCUMENTS

2002/0042147 A1 * 4/2002 Ross et al. .................... 436/174

* cited by examiner

*Primary Examiner* — Jyoti Nagpaul
(74) *Attorney, Agent, or Firm* — Stites & Harbison PLLC; Marvin Petry

(57) ABSTRACT

A histology tissue embedding apparatus having an outlet for embedding medium and a generally horizontal working area beneath the outlet for supporting a cassette. The working area includes a generally horizontal trimming surface having corrugations and being substantially flush with the remainder of the working area.

4 Claims, 9 Drawing Sheets

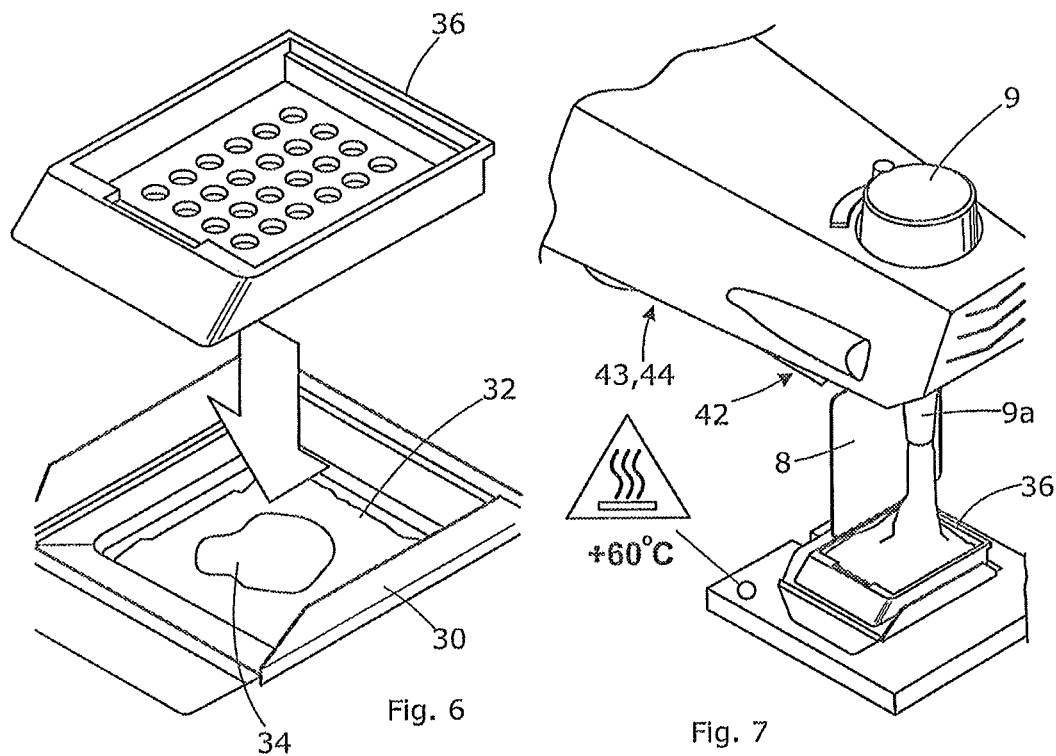
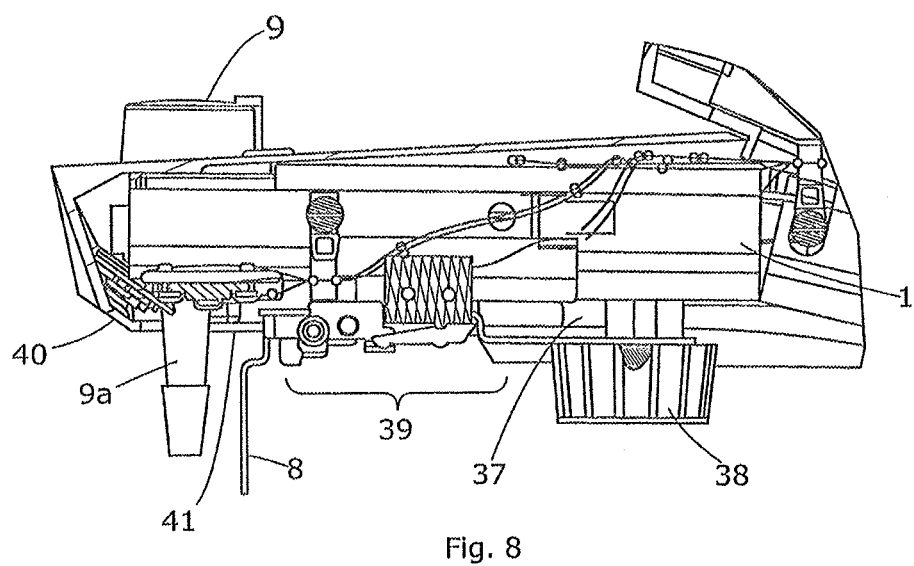

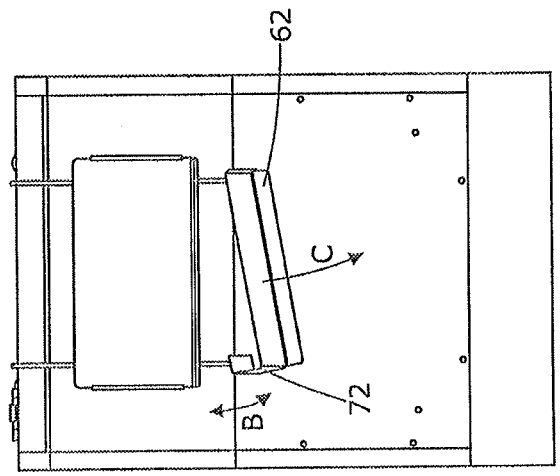
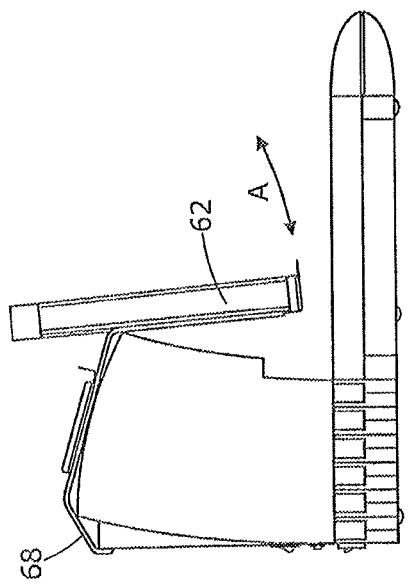
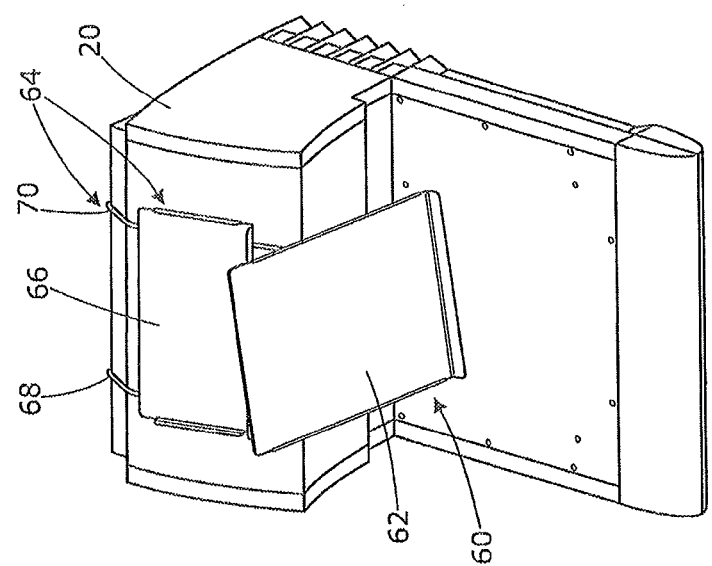

APPARATUS FOR EMBEDDING TISSUE SAMPLES

The present invention relates to an apparatus for embedding tissue samples, typically for histological or histopathological examination.

When tissue samples are collected, it is common to fix the samples for more convenient analysis e.g. viewing under a microscope. One method of fixing is by freezing using a cryostat. An alternative is to treat the tissue samples with various fluids and then to embed each sample in a block of paraffin wax. The embedding process includes several steps, such as heating the paraffin wax, placing it and the tissue sample in a suitable container and setting the wax. Laboratory equipment known as an "embedding centre" is typically used to carry out these processes and the present invention is primarily concerned with providing an embedding centre incorporating one or more improvements.

A tissue embedding centre will generally include a reservoir for the molten paraffin wax and a nozzle connected to the reservoir through which the molten wax can be dispensed into a mould. It is known to include a trigger in the form of a paddle adjacent to the nozzle for control of the wax through the nozzle. Typically, the paddle will be located behind the nozzle (i.e. on the opposite side to the equipment operator) and pressure on the paddle to push it away from the nozzle will operate the nozzle so as to dispense the wax. The paddle is biased to return to a rest position i.e. if there is no operator pressure on it then it returns to the rest position, in which the nozzle is controlled to be closed.

Different equipment operators will use the paddle in different ways e.g. some will operate it by pressing on it with the tissue cassette and others by pressing on it with one of their hands. This can mean that the embedding centre equipment is easier to use for some operators than others. Generally, one aim of the present invention is to provide an adjustable paddle i.e. a paddle (or other wax dispenser control mechanism) whose rest position relative to the nozzle (or other wax dispensing outlet) is adjustable.

Accordingly, in a first aspect, the present invention provides a histology tissue embedding apparatus including a reservoir for an embedding medium and an outlet valve connected to the reservoir through which the embedding medium is dispensable, and including trigger means which control the operation of the outlet valve, the trigger means having a rest position in which the outlet valve is closed, wherein the rest position of the trigger means in relation to the outlet valve is adjustable. In this way, the position of the trigger means can be varied to suit different operators of the equipment.

Preferably the embedding apparatus will include heating means which are usable to heat the reservoir so as to maintain the embedding medium (e.g. paraffin wax) in a molten, liquid, state and the reservoir will be heated so as to be usable. Preferably the outlet valve is a nozzle, which may be oriented substantially vertically so as to dispense the embedding medium into a mould held beneath the nozzle.

Preferably the trigger means is a paddle, which may be located substantially behind the nozzle (from the equipment operator's perspective) as described above. Preferably the rest position of the trigger means is adjustable in a direction away from the outlet valve e.g. so as to create more space between the trigger and the outlet valve.

In some embodiments, a portion of the trigger means is slidably attached to a body of the embedding apparatus. Preferably, the trigger means also includes a locking means (e.g. a locking screw) to retain it so that it is not slidable under normal user operation of the trigger when the locking means is locked, but when the locking means is unlocked the trigger is slidable so as to adjust its position.

One further problem with some existing tissue embedding machines is that the working areas may be poorly illuminated, or the illumination lamps provided may be such that they get in the way of the equipment operator.

Accordingly, in a further aspect, the present invention provides a histology tissue embedding apparatus including an equipment housing having an outlet valve for dispensing a tissue embedding medium into a tissue mould and a working area below the nozzle in which the operator holds a tissue mould in use, wherein the working area also includes a separate cold area which is coolable using cooling means to a temperature suitable for setting embedding medium, wherein the equipment housing incorporates one or more LED lights to illuminate both the working area and the cold area. The use of dedicated LED lights in this way provides both a better quality of lighting and also a less intrusive lighting apparatus.

In use, once a tissue mould has been filled with the embedding medium (which will typically be paraffin wax and which will be referred to as such from now on although other embedding media are also intended to be included), typically some of the wax will be in unwanted areas e.g. overflowing the tissue cassette and/or mould and stuck to its sides.

Accordingly, in a further aspect, a histology tissue embedding apparatus of the present invention includes trimming means for trimming the embedding medium from a cassette. Preferably, the trimming means incorporates a trimming surface, which includes a plurality of corrugations which, when a cassette is rubbed across the surface by a user, help to remove excess embedding medium. Preferably the corrugated surface is heated so as to further facilitate the removal of the excess embedding medium.

In some embodiments of the invention, the trimming means is incorporated into a working surface of a part of the equipment, such that the trimming surface is substantially flush with the surrounding working surface. This means that when not in use the trimming means does not effectively interfere with the user's operation of the equipment and can function as a normal part of the working surface.

Periodically, it is desirable to drain the paraffin wax from known embedding equipment. Generally, this can be a tricky and messy task. The applicant's own prior art embedding equipment is provided with a drain tube through which the paraffin wax may be drained into a suitable receptacle. However, such drain tubes have a tendency to get clogged-up.

Therefore, in a further aspect, the present invention provides a histology tissue embedding apparatus which incorporates a removable embedding medium waste receptacle which, in use, collects excess embedding medium from e.g. the working surface of the equipment during the normal embedding process. In addition, the apparatus may be provided with drainage means via which embedding medium is drainable from the reservoir. The outlet of the drainage means is preferably directed into the location of this receptacle. However, to facilitate the collection of a large quantity of waste, embodiments of the invention may further be provided with an interchangeable, larger, waste receptacle which is attachable to the apparatus in place of the normal waste receptacle. This simple and convenient system allows the embedding medium to be drained without the need for separate reservoir drainage tubes etc as in the prior art equipment. It also preferably conveniently overhangs the bench in front of the instrument.

In a yet further aspect, the present invention provides a histology tissue embedding apparatus incorporating document holding means, which are usable to hold documents required by the equipment operator. Preferably the document holding means are movable from an open position in which they are available to hold a document as described, and a closed position in which they are less obtrusive to the operator of the equipment than when in the open position.

Embodiments of the invention may incorporate any one or some or all of the above aspects, together with any one or some or all of the features described below.

Embodiments of the present invention will now be described with reference to the accompanying drawings in which:

FIG. 6 shows a tissue cassette and mould for use with the present invention.

FIG. 7 shows the operation, of an embodiment of the tissue embedding medium dispenser according to the present invention.

FIG. 8 is a cross-sectional view through a part of an embodiment of the present invention to illustrate the tissue embedding medium dispenser.

FIGS. 12-14 show views of a further embodiment of a document holder in accordance with aspects of the present invention, in this example mounted on a cold module.

FIG. 1 shows a histology tissue embedding system incorporating aspects of the present invention. The system consists generally of a heated module (shown in FIG. 1) and a cold module (shown attached to the heated module in FIG. 2).

The function of the heated module is primarily to dispense a tissue embedding medium (in this case paraffin wax, but other suitable media may be used) into tissue moulds and to provide storage for the various items used. The primary function of the cold module is to cool the tissue moulds after dispensing so that the wax sets.

Figure 1:
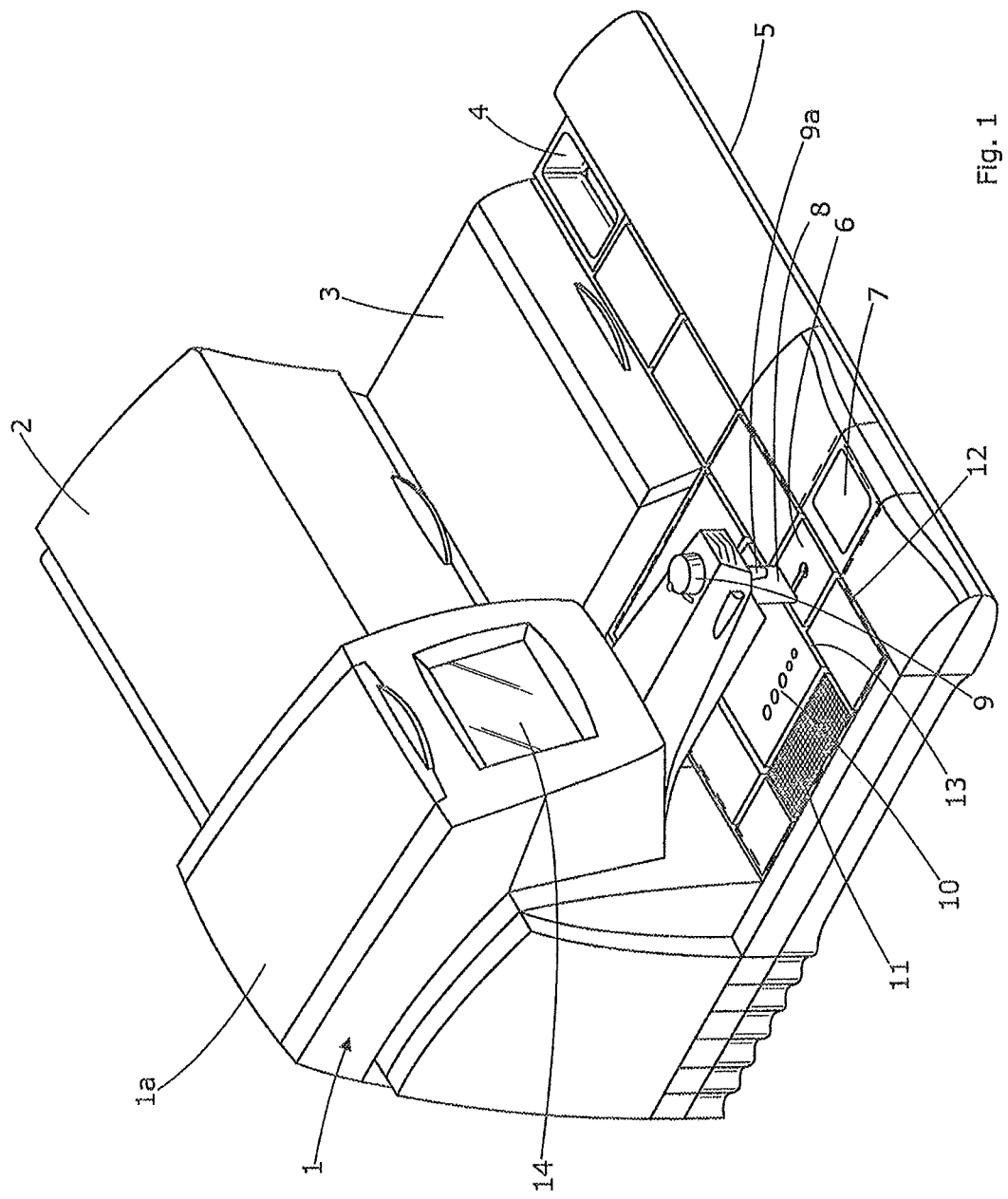
FIG. 1 is a perspective view of a histology tissue embedding centre incorporating aspects of the present invention.

The tissue embedding apparatus shown in FIG. 1 includes a tank 1 for the wax. The tank 1 is heated by suitable heating means (not shown) in order to raise the temperature of the wax so that it is in liquid form for dispensing. Wax is added to the tank via lid 1a. The apparatus includes a base mould storage compartment 2 for storing the base moulds into which wax will be poured, and a tissue storage tank 3 for storing tissue samples in the respective cassettes. There is also a cassette lid storage dish 4 located adjacent the tissue storage tank 3.

In use, liquid wax is dispensed from the wax tank 1 via an outlet valve, which includes nozzle 9a. The rate of dispensing of the nozzle is controlled by a wax dispense flow control 9 and the operation of the nozzle is controlled by a trigger means, which in this example is a dispense lever 8. When the dispense lever 8 is in its rest position, the nozzle is closed and no wax is dispensed. However, when the wax dispense lever is pressed by the operator away from the nozzle 9a (i.e. towards the tank 1), the nozzle is opened and wax is dispensed in accordance with the setting of the wax dispense flow control 9.

In use, a base mould will be held underneath the nozzle 9a, on top of a hot spot plate 6. The hot spot plate is heated by further heating means (not shown) which helps to prevent the wax from solidifying too quickly once it has been dispensed into the base mould.

Adjacent the hot spot plate 6 is a cold spot plate 7, which is cooled by cooling means (not shown). After wax has been dispensed into the base mould, the base mould may be placed by the operator on cold spot plate 7 to increase the rate of solidification of the wax. Once the wax has substantially solidified, excess wax may be removed by the operator using wax trimmer 11.

The general working area of the equipment, for use by the operator, is enclosed by dashed line 12 i.e. incorporates the wax trimmer 11, the hot spot plate 6, the cold spot plate 7, and other areas for the placement of cassettes etc. In addition, there is a separate work surface 20, for example, for storage of the operator's forceps.

Waste wax accidentally dropped onto the working area 12, and other areas, is collected via a series of grooves and channels in the working area (one example is identified with numeral 13) and is collected in a waste wax tray 5 which will be described in more detail later.

Figure 2:
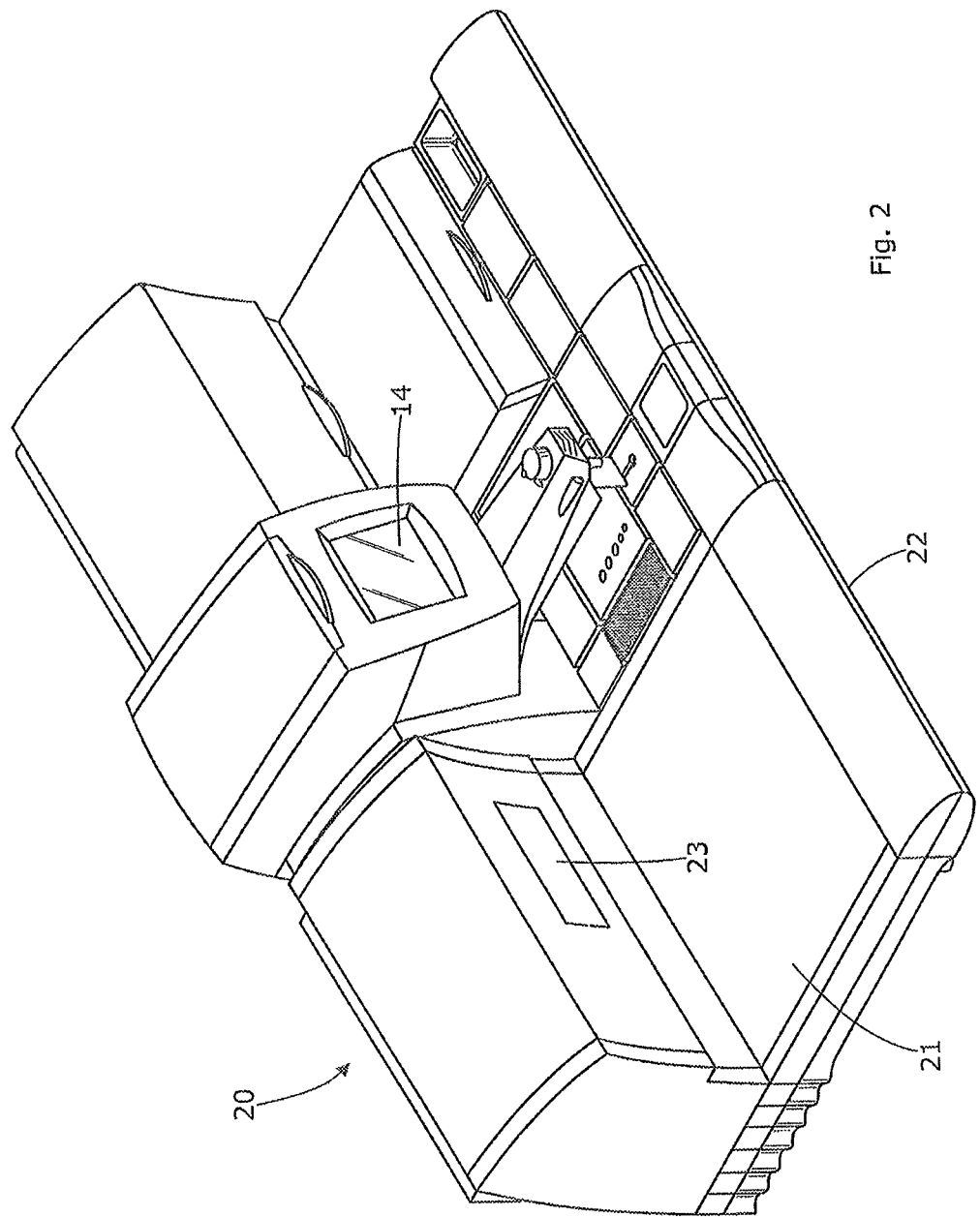
FIG. 2 shows the apparatus of FIG. 1 further including a cold module according to aspects of the present invention.

FIG. 2 shows the apparatus of FIG. 1 with the addition of a cold module, identified generally with reference numeral 20. The cold module incorporates a large cold plate 21, which is useable to cool a number of base moulds. In addition the cold module incorporates a storage drawer 22 for further equipment storage.

An additional feature of some embodiments of the invention is document holding means, which in this embodiment is provided by an openable tray 23. The tray 23 is movable between a closed position (shown) in which it is substantially flush with the surrounding surface of the equipment, so as to be unobtrusive, and an open position in which it is usable to hold a document for the operator. A further embodiment of a document holder will be described later.

More and more use of printed lists of notes and information about specimens is being provided to assist the embedding process. Traditionally, these notes were placed near to the embedding centre or on any convenient surface that they could rest on. However, these positions were not typically in the correct place to allow the user to readily see the notes. The incorporation of a document holder into the embedding centre (in this example mounted on the cold stage module) allows the user to view and if necessary mark up the notes with minimum interruption to the embedding process.

The apparatus is controlled by a control system (not shown) and the user-operable functions are accessed by means of a touch screen 14.

Figure 3:
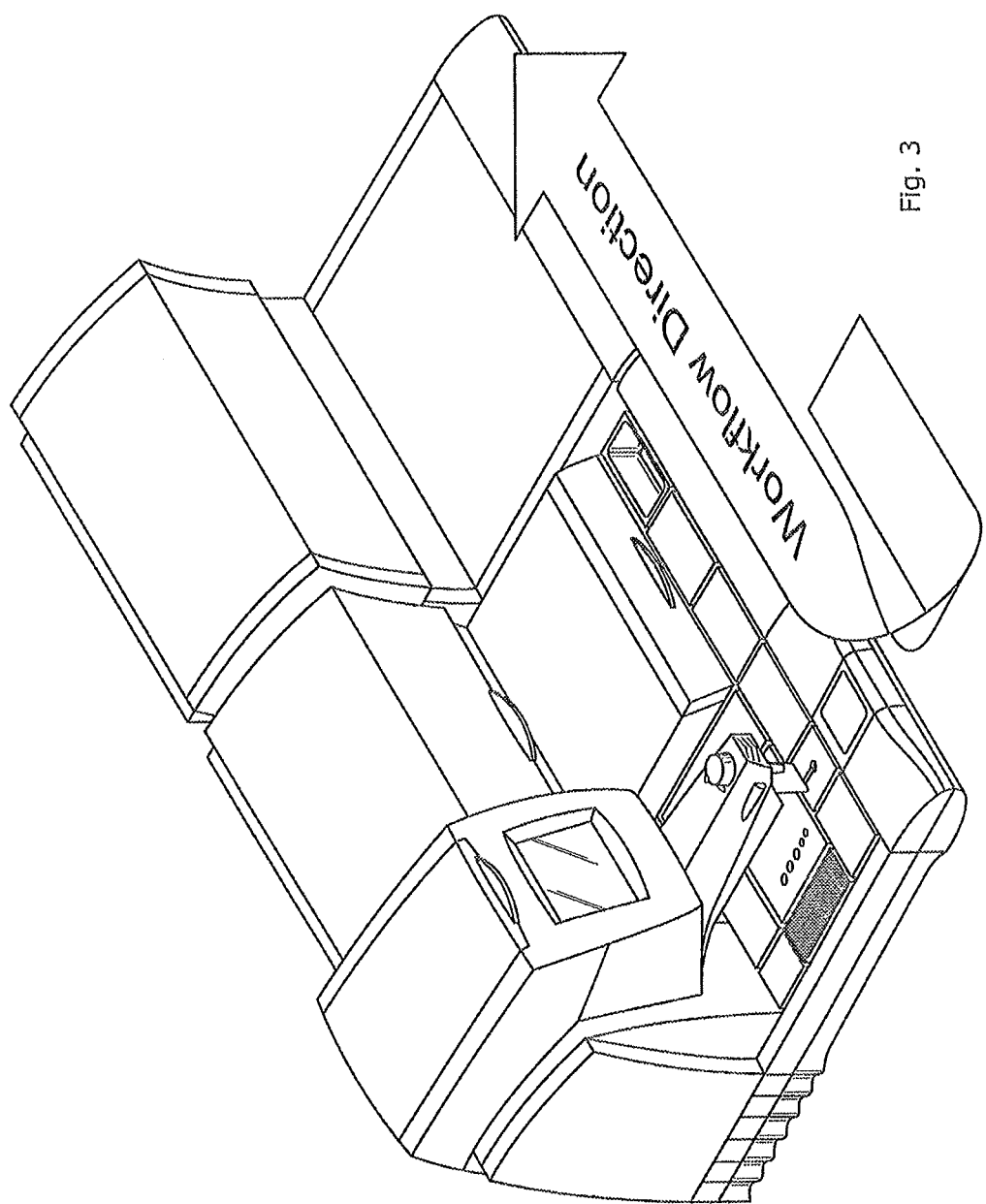
FIGS. 3-5 show variations on the apparatus of FIGS. 1 and 2 to illustrate how the apparatus may be used in practice.
Figure 4:
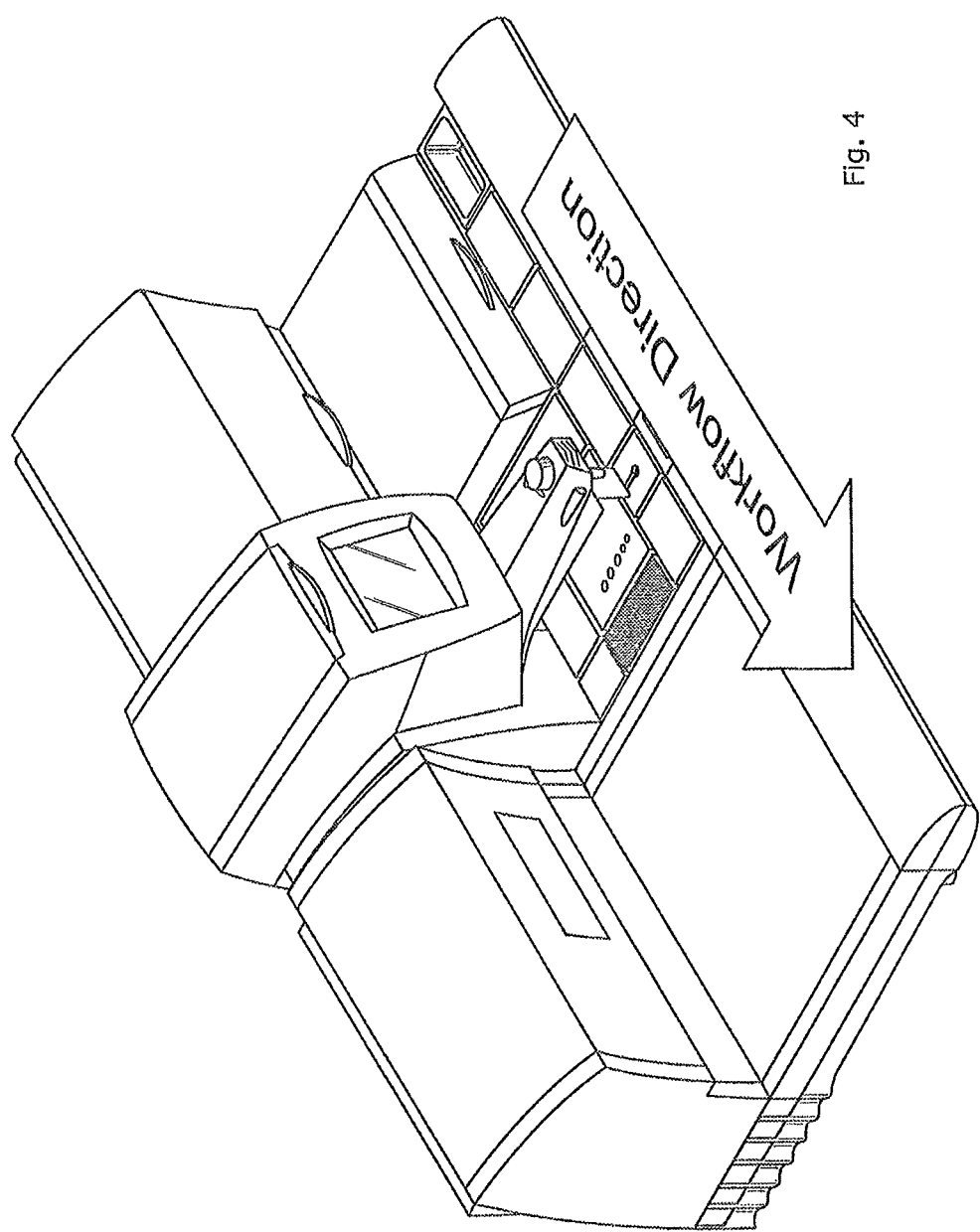
Figure 5:
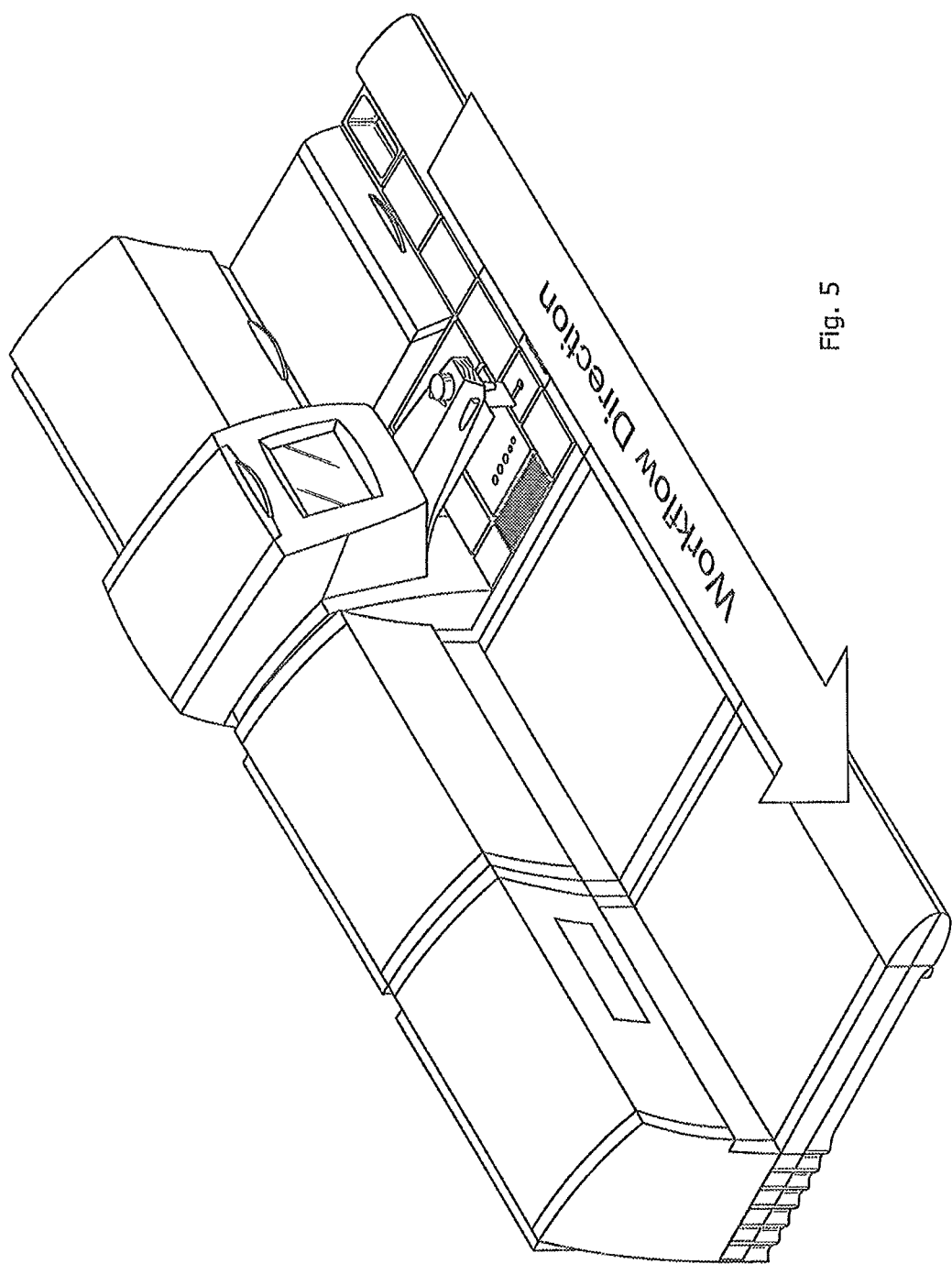

In use, the apparatus according to the present inventions may be operated in various ways, depending on user preference. FIGS. 3 to 5 show three different options. In FIG. 3, moulds and cassettes will be taken from the centrally located storage areas, processed by filling with wax on the left of the equipment, and then moved to the right-most end for the cold storage module. An alternative is shown in FIG. 4, where the cold storage module is located on the left hand side of the paraffin wax dispensing part of the apparatus. A further option is shown in FIG. 5, where the apparatus includes an additional cold storage module, for further capacity.

As mentioned previously, the embedding process typically causes some excess wax to be left on the outer face of the cassette and/or mould which needs to be removed so it can be clamped firmly during the subsequent sectioning process. Traditionally this is done manually using a thin blade to scrape excess wax from the cassette faces.

The wax trimmer device improves this process. A series of grooves (e.g. square but could be other shapes such as triangular, saw tooth etc) are in a metal plate that is heated to about the wax melting temperature. The face of the cassette can then be rubbed across these grooves which causes the wax to be removed. The device is incorporated into the embedding module so that cassettes can be fully prepared and finished on the one instrument rather than having to trim at a later stage in the process. An additional benefit is that the wax trimmer forms part of the embedding deck and is preferably flush with it, and it can continue to be used for normal embedding activities, thus keeping space to a minimum.

FIGS. 6 to 8 illustrate generally the filling of a mould with wax. FIG. 6 shows a base mould 30 into which some wax 32 is placed. The tissue specimen 34 is placed on top of the lower layer of wax 32 and the base mould is moved on to the cold spot plate, typically until the wax becomes translucent. Following that, the tissue cassette 36 is placed into the base mould 30, on top of the sample 34 and the cassette is filled with wax via the nozzle 9a as shown in FIG. 7.

As previously described, the operation of nozzle 9a is controlled via dispense lever 8. FIG. 8 shows a cross-sectional view through the portion of equipment including the wax tank and nozzle dispensing system.

Users will actuate the lever 8 by a variety of means e.g. finger, forceps, embedding mould. They may also be working with different size cassettes and moulds. Adjustment of the distance from the lever to the nozzle allows the user to set the distance optimally to suit their needs.

Traditionally, the lever position is fixed relative to the nozzle.

A knob 38 behind the lever is used to release it, which is then adjusted before locking in position. The lever assembly 39 is mounted on a slideway 37 to allow the adjustment. Different locking methods could be used and/or with one or more pre-defined positions.

Tissue samples can be quite small, and orientation of the sample can also be important. The placement process is manually carried out by an operator using forceps so good illumination of the working area is important. Traditionally there was some basic illumination mounted next to the dispense nozzle and then supplementary illumination provided by a light on a flexible arm that could be directed as required by the user. However, this extra light could also get in the way of the operator as the embedding process is a very manual process.

The invention provides for one or more (in this case 3) of high intensity LED lights, 40, 41, 42, mounted in front of and to the sides of the dispense nozzle. They are preferably angled to provide a full area of illumination both under the nozzle and spreading out over the wider working area. In addition one or more (2 in this case) LED lights, 43, 44 are mounted further back on the instrument structure to provide more general illumination of the working area.

This combination of lights provides good illumination over the full working area without any obstructions to the user, or the need for different users to adjust the position of the flexible light for their own individual preference.

Figure 9:
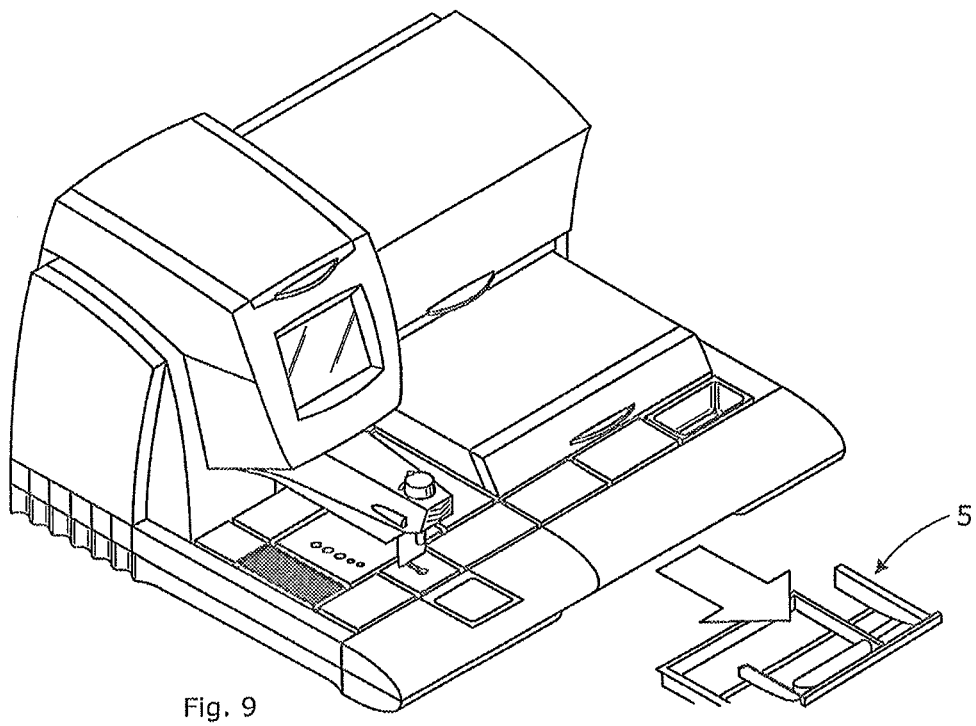
FIGS. 9 and 10 illustrate embodiments of the invention incorporating an embedding medium drainage module.
Figure 10:
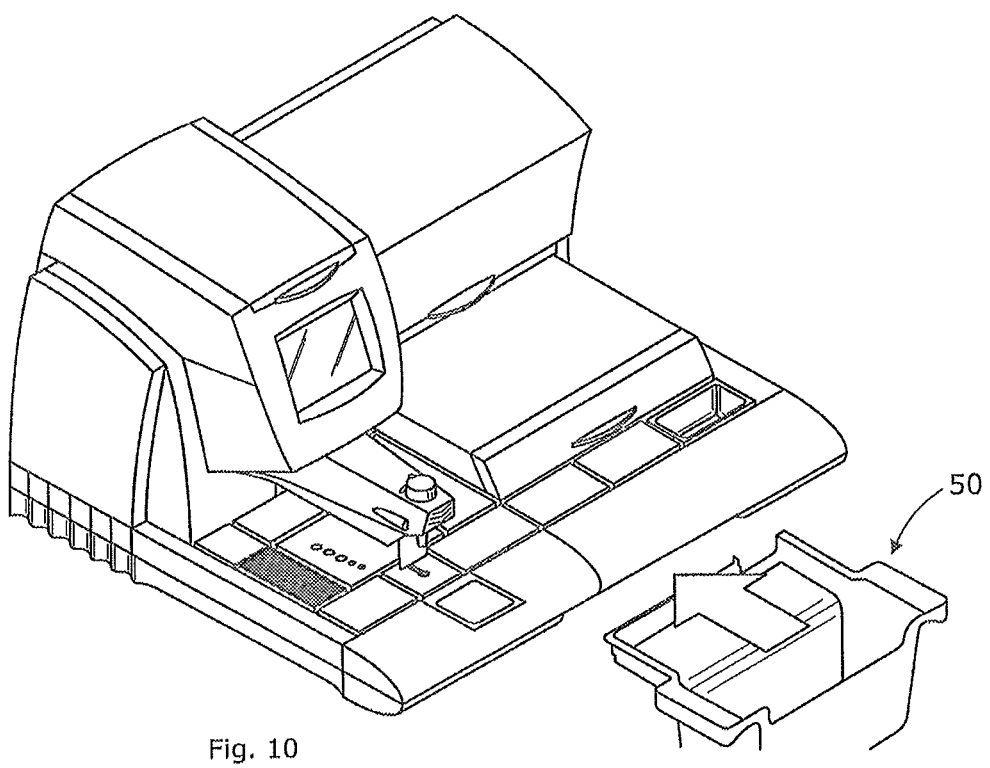
Figure 11:
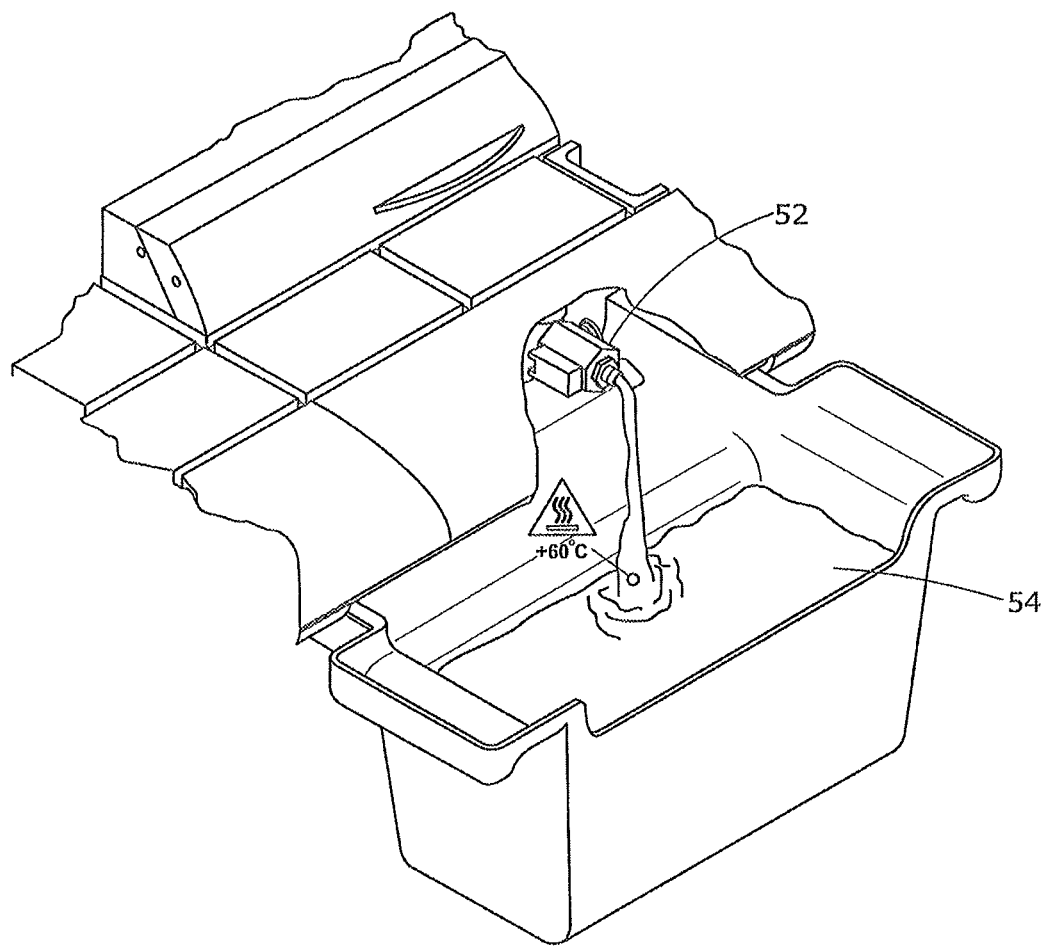
FIG. 11 shows the operation of the embedding medium drainage module of FIG. 10.

FIGS. 9 to 11 show the aspects of the present invention relating to drainage of the embedding medium from the equipment.

Molten wax is a difficult substance to work with and dispose of. Once it is removed from the heated storage area it can start to solidify on the surface and can block drain pipes, tubes or other devices. It can also be difficult to drain into waste bags.

The embedding centre has a small wax waste drawer 5 that collects excess wax during the normal embedding process. To fully drain the wax, the waste drawer 5 is removed and replaced with an enlarged container 50 that hangs over the front of the bench. Preferably, this container mounts in the same guides as the wax waste drawer. Once drained, the waste container can be easily removed and the wax disposed of.

FIG. 11 shows drainage nozzle 52 used to drain the wax 54 from the tank/reservoir 1.

FIGS. 12-14 show a further example of a document holder in accordance with aspects of the present invention. In this example, the document holder (indicated generally by reference numeral 60) is shown attached to a cold module 20. However, the document holder 60 may equally be attached to a hot module, or indeed any other part of an embedding centre.

The document holder 60 includes a document support 62 on which, in use, a document will be placed. The document holder 60 also includes attachment means, identified generally by the numeral 64. In this example, the attachment means 64 include a plate 66 which rests generally on top of a part of the cold module 20, and (68), (70) which help to secure the document holder to the cold module. Other attachment means may of course be used.

One of the preferred features of a document holder according to the present invention is that while fixed in place on a part of the embedding centre, the orientation of the document support 62 may be adjusted with respect to the embedding centre. In this example, the attachment means are such that the document tray 62 may preferably be tilted forwards and backwards i.e. in the direction of the arrow A shown in FIG. 13. Additionally or alternatively, the attachment means are such that the document tray 62 may be adjusted from side to side i.e. in the direction of the arrow B shown in FIG. 14. The side to side adjustment is such that the document faces in a direction towards an operator located not directly in front of the part of the embedding centre on which the document holder is mounted, for example in the direction of arrow C shown in FIG. 14. In the particular example shown in FIG. 14, this is achieved by an adjustable side member 72, which increases the spacing of one side of the document tray 62 from the part of the embedding centre on which it is mounted. Other means to achieve the same result may of course be used.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

The invention claimed is:

1. A histology tissue embedding apparatus comprising:
   an outlet for embedding medium,
   a generally horizontal working area located below the outlet for supporting a cassette which is positioned to receive embedding medium from the outlet, in which area processing of the contents of the cassette takes place,
   the working area including a generally horizontal trimming surface which includes corrugations and which is substantially flush with the remainder of the working area,
   wherein moving a cassette generally horizontally from the working area across the trimming surface helps to remove excess embedding medium from the cassette.

2. An apparatus according to claim 1, including a heater which heats the corrugated surface to further facilitate removal of the excess embedding medium.

3. An apparatus according to claim 1, wherein the working area includes a separate work surface and the trimming surface is adjacent the separate work surface.

4. An apparatus according to claim 1, wherein the working area includes a hot area located beneath the outlet, a cold area located adjacent the hot area and a separate work surface located on the side of the hot area opposite from the cold area, and the trimming surface being located adjacent the separate work surface.

* * * * *